United States Patent
Toussaint Nasta et al.

(10) Patent No.: US 10,206,628 B2
(45) Date of Patent: Feb. 19, 2019

(54) METHOD TO OBTAIN AND VALIDATE PHYSIOLOGICAL DATA

(71) Applicant: GENOMI-K S.A.P.I. DE C.V., Monterrey (MX)

(72) Inventors: Francisco Xavier Toussaint Nasta, Monterrey (MX); Hector Cruz Camino, Monterrey (MX); Hector Daniel Guerrero Marquez, Monterrey (MX); Rene Daniel Gomez Gutierrez, Monterrey (MX); Ricardo Mendoza Gonzalez, Monterrey (MX); Roberto Carlos Arriaga Sosa, Monterrey (MX); Roberto Mercado Hernandez, Monterrey (MX)

(73) Assignee: GENOMI-K. S.A.P.I. DE .C.V., Monterrey (MX)

(*) Notice: Subject to any disclaimer, the term of this patent is extended or adjusted under 35 U.S.C. 154(b) by 331 days.

(21) Appl. No.: 15/262,456

(22) Filed: Sep. 12, 2016

(65) Prior Publication Data

US 2017/0224285 A1 Aug. 10, 2017

(51) Int. Cl.
A61B 5/1455 (2006.01)
A61B 5/00 (2006.01)
A61B 5/026 (2006.01)
A61B 5/024 (2006.01)

(52) U.S. Cl.
CPC ............ *A61B 5/7221* (2013.01); *A61B 5/024* (2013.01); *A61B 5/0261* (2013.01); *A61B 5/14551* (2013.01)

(58) Field of Classification Search
CPC . A61B 5/0205; A61B 5/1455; A61B 5/14551; A61B 5/14552; A61B 5/0261; A61B 5/7221; A61B 5/024
See application file for complete search history.

(56) References Cited

U.S. PATENT DOCUMENTS

| | | | | |
|---|---|---|---|---|
| 5,485,847 A * | 1/1996 | Baker, Jr. | ........... | A61B 5/14551 600/323 |
| 6,334,065 B1 * | 12/2001 | Al-Ali | ................ | A61B 5/14551 600/323 |
| 8,457,707 B2 * | 6/2013 | Kiani | ................ | A61B 5/02416 600/324 |

(Continued)

OTHER PUBLICATIONS

"Electromyographic signal processing and analysis methods", Gila et al., 2009, vol. 32, Supplement 3, p. 27-43.

(Continued)

*Primary Examiner* — Eric Winakur
*Assistant Examiner* — Chu Chuan (JJ) Liu
(74) *Attorney, Agent, or Firm* — Young & Thompson

(57) ABSTRACT

A method for the validation of physiological data, acquired in two or more parts of the human body by sensors connected to a medical device, for the statistical validation of the relationship among the signals retrieved by the medical devices, in order to select information that increases the accuracy of the study being carried out, with a high statistical certainty. The purpose of the actual invention is to make this statistically validated data available for use by protocols or reference values, according to the field of application, which increase accuracy of the studies being carried out.

7 Claims, 2 Drawing Sheets

(56) References Cited

U.S. PATENT DOCUMENTS 9,392,945 B2 * 7/2016 Al-Ali ................ A61B 5/14551
2016/0045117 A1 * 2/2016 Liu ..................... A61B 5/7221
600/485

OTHER PUBLICATIONS

"Strategies for Implementing Screening for Critical Congenital Heart Disease", Kemper et al., Pediatrics vol. 128, No. 5, Nov. 2011.
"Measurement and Interpretation of the Ankle-Brachial Index", A Scientific Statement From the American Heart Association, Aboyans et al., Circulation Dec. 11, 2012.

* cited by examiner

Flow diagram showing the critical congenital heart defects screening protocol adopted by the American Academy of Pediatrics.

METHOD TO OBTAIN AND VALIDATE PHYSIOLOGICAL DATA

BACKGROUND OF THE INVENTION

A. Field of the Invention

The actual invention includes methods for the validation of physiological data, acquired in two or more parts of the human body by sensors connected to a medical device, for the statistical validation and comparison of the relationship among the signals retrieved by said medical devices, in order to select information that increases the accuracy of the study being carried out. The purpose of the actual invention is to make this data available for use by protocols or reference values, according to the field of application.

B. Background of the Invention

One of the concerns of the people involved in the health sector is the reliability of the results provided by medical devices using physiological data acquired in two or more parts of the human body. This is due to the fact that most of the values visually retrieved by the operator through a medical device interface are not filtered to distinguish between reliable values and values resulting from errors in measurements, in addition to the absence of a reliable comparison between the data acquired by sensors in two or more parts of the body.

This means that the statistical certainty of the study decreases if data collection is made visually and the information is not statistically validated to make sure that the acquired physiological data is comparable.

Additionally, the time spent in acquiring said data and the amount of analyzed data vary and are contingent upon the operator's experience and criteria. In other words, the operator decides the time at which the system stability or data certainty is acceptable and proceeds to obtain the required values. However, this decision is subjective and may lead to errors in the reported results.

A medical device for acquiring physiological data in two or more parts of the human body may be, for example, a physiological monitor for obtaining oxygen saturation values from a patient, where said physiological monitor may comprise: two or more LED light-emitting/receiving sensors connected to a corresponding pulse oximeter at one or more USB communication ports, and a computer in communication with the USB interface. In order to increase reliability of the measurement results of said physiological monitor, it is necessary to validate, firstly by the medical device, that the connections of the pulse oximeter sensors to the computer exist in order to be able to proceed to the retrieval and analysis of physiological data from said locations.

If said validation is not made, measurement anomalies, highly capable of generating low certainty level results and, thus, dubious interferences and potentially erroneous diagnoses, may not be identified.

In view of the needs described above, the applicant has developed a method for the acquisition and validation of physiological data for the incorporation thereof to medical devices, said method allows the comparison of physiological data acquired in two or more parts of the body and the inference of the system stability in order to provide certainty to the results of the study being carried out.

By the use of the method of the actual invention, it is possible to validate and compare the fact that the signals retrieved by medical devices provide data with high statistical certainty.

SUMMARY OF THE INVENTION

Therefore, a main object of the actual invention is to provide a method for the validation of physiological data, acquired in two or more parts of the human body by sensors connected to a medical device, for the statistical validation of the relationship among the data of signals retrieved by said medical devices, in order to select information that increases the accuracy of the study being carried out, with a high statistical certainty.

A further main object of the actual invention is to provide a method for the acquisition and validation of physiological data for the incorporation thereof to medical devices of the nature described above, where said method allows the identification of measurement anomalies highly capable of generating low certainty level results and, thus, dubious interferences and potentially erroneous diagnoses.

An additional object of the actual invention is to provide a method for the acquisition and validation of physiological data for the incorporation thereof to medical devices of the nature described above, where said method comprises the following general steps of: verifying that sensors are connected to the medical device; retrieving physiological information from two or more parts of the human body; verifying that physiological data, consistent with the parameters sought to be measured, is recorded; making a statistical analysis of the physiological data retrieved from said two or more parts of the human body; and using said physiological data, found by the statistical analysis to be suitable, for the use in applications to protocols/reference values.

These and other objects and advantages of the actual invention will be evident to those skilled in the field of application of the invention from the following detailed description.

DETAILED DESCRIPTION OF THE INVENTION

Figure 1:
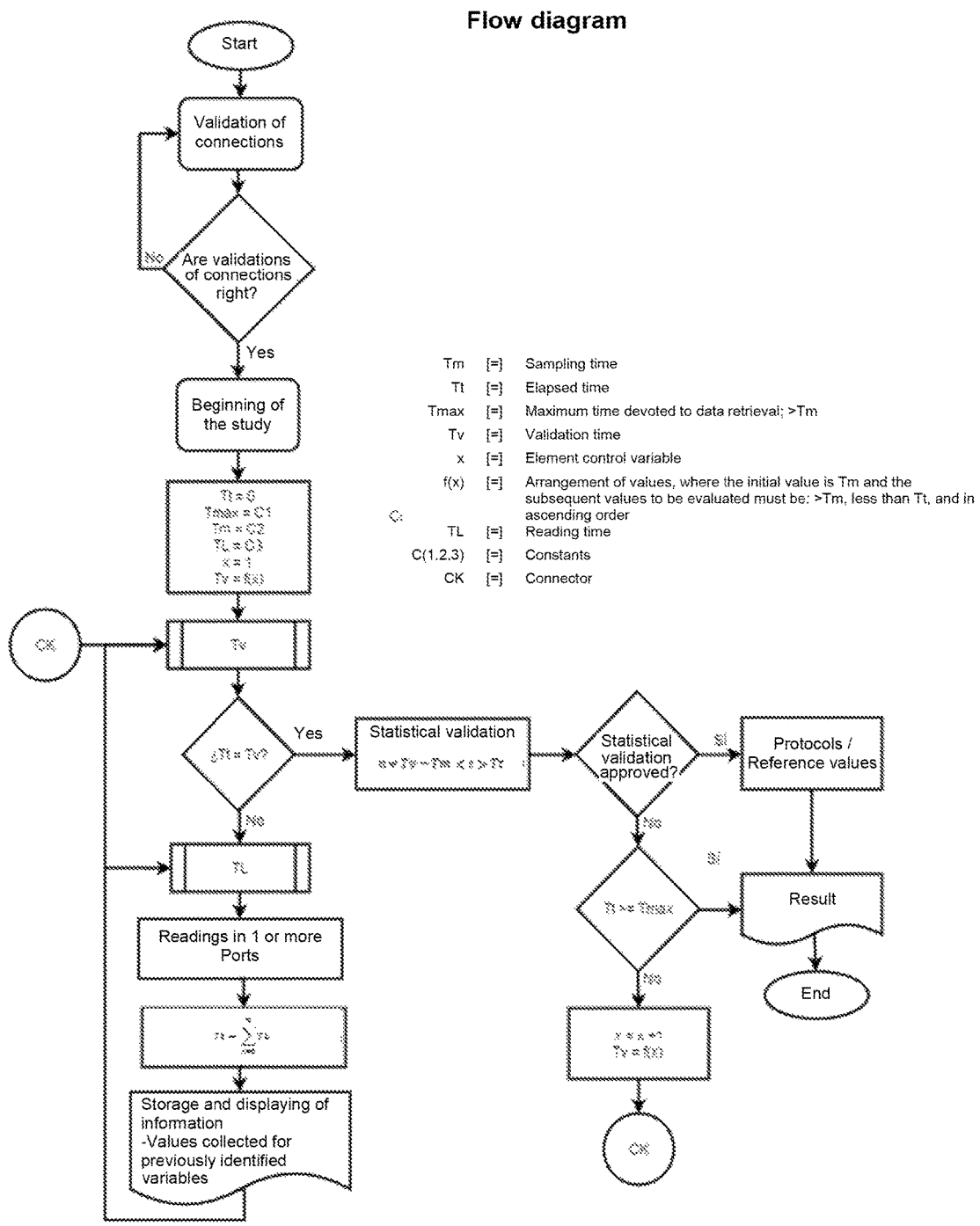
FIG. 1 is a flow diagram of the method of the actual invention.

The method for the acquisition and validation of physiological data, for use thereof with medical devices generally comprising one or more sensors connected to information processing means, comprises, in its more general embodiment, the following steps:

a) verifying that sensors are connected to the medical device by information processing means, and that physiological data, consistent with the parameters sought to be measured, is recorded;

b) defining the elapsed time of the study (Tt; starting at 0 seconds); the maximum time of the study (Tmax=specific time constant); the sampling time (Tm=specific time constant) during which the physiological data, needed for the statistical study, is collected; the reading time (TL=specific time constant), said reading time being the interval at which physiological data is retrieved from the communication port; the validation time (Tv), which defines the time at which statistical analysis is carried out, said validation time comprising one or more preset time values greater than Tm;

c) retrieving physiological data separately from each of said two or more sensors by said information processing means within a preset reading time interval (TL), and hosting and displaying the information of the collected values;

d) repeating step c) every TL until the following condition is met: Tt=Tv. When this condition is met, proceeding to the next step;
e) making a statistical validation of the physiological data retrieved from said two or more sensors, defined based on the volume and characteristics thereof, by the use of the information processing means;
f) if physiological data, acquired in this manner, does not approve step e) and Tt<Tmax, repeating steps c), d) and e);
g) if physiological data, acquired in this manner, does not approve step e), and Tt>=Tmax, generating an "unconcluded data validation" result and concluding the method;
h) if physiological data, acquired in this manner, does approve step e), classifying said acquired data as being suitable for the use in applications to protocols/reference values by information processing means. The application of this data depends on the medical device concerned and on the physiological variables under study by said medical device.
i) generating a result based on step h) and concluding the method.

In a particular embodiment, the method for the acquisition and validation of physiological data of the actual invention, for use thereof with medical devices, may be applied to a physiological monitor for the simultaneous acquisition of oxygen saturation values in the preductal and postductal blood flow from a patient, wherein said physiological monitor may comprise: two LED light-emitting/receiving sensors connected to its pulse oximeter to be placed on two or more parts of the patient's body, wherein each pulse oximeter is connected to information processing means, the method of the actual invention comprising:
a) after placement of the sensors in the subject under study, verifying: that sensors are connected to the medical device, that sensor receptor captures the light signal emitted by the sensor, and that the recorded physiological data is consistent with the heart rate readings;
b) upon successful conclusion of step a), beginning the study and establishing the following variables: elapsed time of the study (Tt; starting at 0 seconds); maximum time of the study (Tmax=specific time constant); sampling time (Tm=specific time constant) during which the physiological data, needed for the statistical study, is collected; reading time (TL=specific time constant), said reading time being the interval at which physiological data is retrieved from the communication port; validation time (Tv), which defines the time at which statistical analysis is carried out, said validation time comprising one or more preset time values greater than Tm;
c) retrieving physiological data (heart rate, oxygen saturation in preductal and postductal blood flow, as well as the values needed to generate a plethysmographic curve) separately from each of said two sensors and stored in the pulse oximeters by said information processing means within a preset reading time interval (TL), with a time difference of about 0.001 seconds between each of them (simultaneously), and hosting and displaying the information of the collected values;
d) repeating step c) every TL until the following condition is met: Tt=Tv. When this condition is met, proceeding to the next step;
e) making a statistical validation of the heart rate values retrieved from said two sensors—said information being stored in the pulse oximeters and retrieved by the information processing means—defined based on the volume and characteristics thereof, and comprising the following sub-steps:
  i. calculating the absolute differences for each record of heart rates comprised within the time interval under analysis;
  ii. obtaining two or more random samples of the maximum absolute differences previously calculated, wherein each sample includes 10% of the population of retrieved heart rate data (n);
  iii. calculating the following statistics for each heart rate data sample: (1) mean difference average ($d_m$), (2) standard deviation ($s_d$), and (3) t value (of the statistical test known as t-Student) for each sample ($\tau$) taken in sub-step ii, in accordance with the following formulas:

$$d_m = \left| \frac{\sum_{i=1}^{n} d_i}{n} \right| \quad (1)$$

$$s_d = \sqrt{\frac{\sum_{i=1}^{n} (d_i - d_m)^2}{n-1}} \quad (2)$$

$$\tau = \frac{d_m}{s_d} \sqrt{n} \quad (3)$$

iv. applying the following conditions: $d_m$<'preset value' and $s_d$<'preset value', wherein said preset values for the present particular embodiment of the invention are: $d_m$<4.602 beats/minute and $s_d$<4.718 beats/minute;
  v. If the established conditions are met in sub-step iv, comparing the $\tau$ value (calculated in sub-step III) to the t value in the t-Student test table; where, if $\tau$>2.55, it can be concluded that there is not a significant difference between the preductal and the postductal blood flow (99% certainty); that is, heart rates are statistically similar and, therefore, the analyzed heart rate data samples are considered as having approved the statistical validation; otherwise, the analyzed heart rate data samples are considered as having failed the statistical validation.
f) if heart rate data, acquired in this manner, does not approve step e) and Tt<Tmax, repeating steps c), d) and e);
g) if heart rate data, acquired in this manner, does not approve step e), and Tt>=Tmax, generating an "unconcluded data validation" result and concluding the method;
h) if heart rate data, acquired in this manner, does approve step e), classifying said data as being suitable for the use in applications to a critical congenital heart defects screening protocol by information processing means;
i) generating a result based on step h) and concluding the method.

Additionally, the statistically validated measurement values may be automatically stored in the information processing means memory and hosted in an external server for further consultation thereof. From said measurement values, operational and medical reports and informative sections may be generated.

Among the reports that may be generated by information processing means, supplementary information regarding said values may be found, which depends on the values obtained by the application of physiological data to protocols/reference values, on the statistical validation, on the physiological variables under study, on the medical device, and on the medical protocols to be incorporated.

Figure 2:
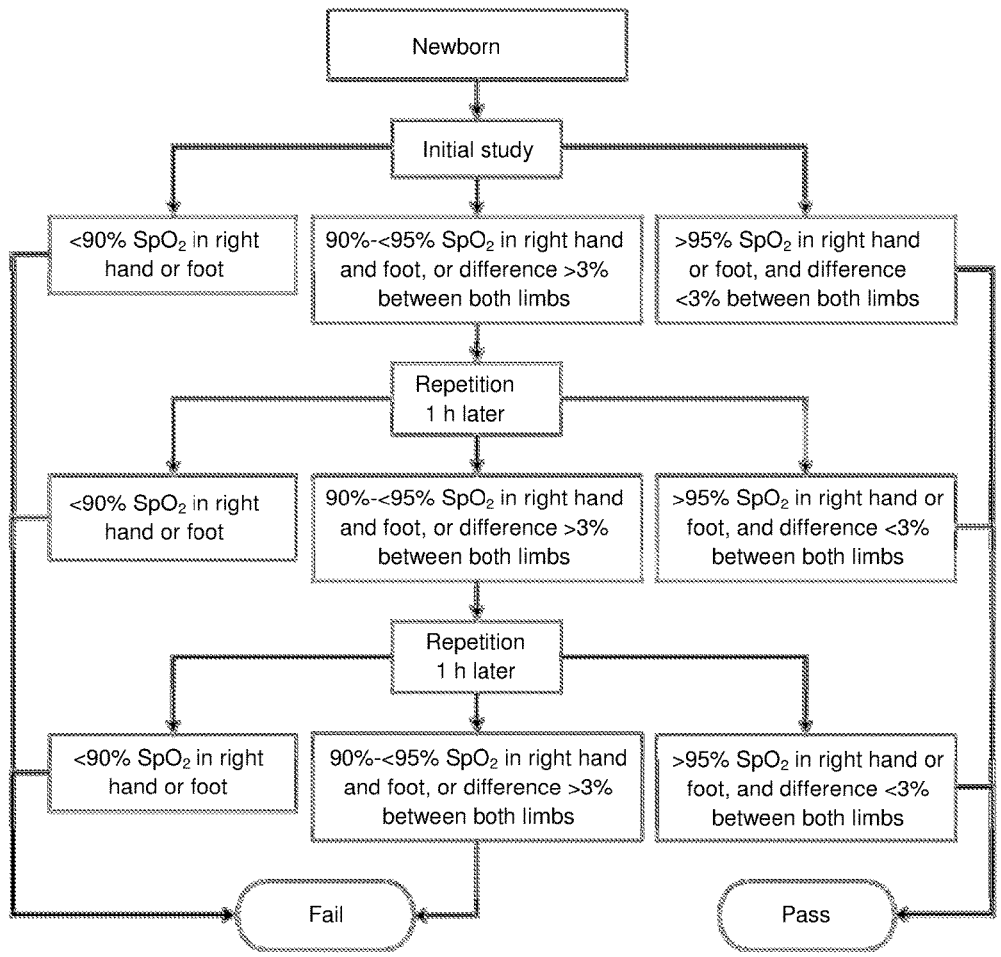
FIG. 2 is a flow diagram of a heart defects screening protocol.

For instance, the values obtained may comprise oxygen saturation in preductal and postductal blood flow of a newborn, and said values may be assessed by information processing means applying said values to the critical congenital heart defects screening protocol [1] defined by the American Academy of Pediatrics, represented by the flow diagram of FIG. 2.

The results obtained by the application of the protocol may be processed together with the oxygen saturation values obtained from preductal and postductal blood flow and from the differences between them to issue a conclusion in accordance with the following table:

| Study | Oxygen Saturation (SpO$_2$) | | | SpO$_2$ Difference Hand and Foot | Result | Conclusion |
|---|---|---|---|---|---|---|
| | Hand | | Foot | | | |
| 1, 2 or 3 | >=95% | or | >=95% | and <=3% | "Pass" | The newborn approved the cardiac screening. Concluded protocol. |
| 1, 2 or 3 | <90% | or | <90% | — — | "Fail" | Immediately remit the newborn to Neonatology and/or Pediatric Cardiology for assessment |
| 1 | 90%-<95% | and | 90%-<95% | or >3% | "Fail": | Repeat the study 1 hour later |
| 2 | 90%-<95% | and | 90%-<95% | or >3% | "Fail": | Repeat the study 1 hour later |
| 3 | 90%-<95% | and | 90%-<95% | or >3% | "Fail": | Immediately remit the newborn to Neonatology and/or Pediatric Cardiology for assessment. |
| Unconcluded | — | — | — | — — | "Unconcluded" | A successful statistical validation was not obtained. |

Because the retrieval of physiological data in step c) is made separately for each pulse oximeter, with a time difference between readings of about 0.001 seconds, a simultaneous data reading in both parts of the body may be considered as being made, whereas in other embodiments of the invention simultaneous data readings may be achieved (with a time difference between readings of about 0 seconds) in two or more parts of the human body.

In the application of the particular embodiment described above, steps c), d), and e) are carried out until a maximum elapsed time (Tt) of 2 minutes and 10 seconds. Each second the information processing means retrieve 75 readings from the pulse oximeter (4,500 records/minute), including values of: heart rate, oxygen saturation in preductal and postductal blood flow, and the values needed to generate a plethysmographic curve. The statistical validation is carried out a maximum of six times within the elapsed period in a constant physiological data range (Tv–Tm→Tt); i.e. $f(x)=\{x \in N: x<=x=Tt\}$; $x=\{60, 70, 80, 95, 110, 130\}$.

This method provides high certainty that measurement of oxygen saturation in preductal and postductal blood flow was made under the same circumstances, and that the acquired physiological data is representative of the condition under study. Moreover, measurement of physiological data is standardized in all individuals.

In the event that any of the samples fails to meet the conditions prior to the t-Student test or the t-Student test itself in any of the 6 times, including the condition described in step f), the study is considered as being unconcluded for the statistical validation.

While it was mentioned that the statistical validation step uses the t-Student statistical test, it should be understood that any other parametric statistical test, such as Z-score normal distribution, Student-Welch T-test, chi square test or F test, might be used.

Moreover, the method of the actual invention may be used for the validation of physiological data acquired in two or more parts of the human body.

Thus, the method of the actual invention provides the following advantages:

- Standardization of the number of analyzed physiological data by virtue of the definition of a time interval or amount of data that provides the generation of representative samples.
- Initial verification that the emission/receipt is being carried out by sensors and that the continuity of the signal transmitted by these sensors to the medical device allows making certain that suitable data is being acquired.
- Analysis of the same physiological moment in consideration of the data reading simultaneousness in one or more parts of the human body (of preductal and postductal blood flow in the particular embodiment described herein).
- Auto-verification that readings of physiological data acquired in one or more parts of the body (of the preductal and postductal blood flow in the particular embodiment described herein) are statistically comparable.
- The physiological data, acquired from the measurement device (the pulse oximeter in the particular embodiment described herein), is stored in a database, allowing for further consultation and management thereof for the generation of reports of incidences, statistics and operational control.

Example

From the 4,500 records (heart rate in two parts of the body, one preductal and the other postductal) captured by each pulse oximeter (two in total) within an 1-minute interval (Tm), a random sampling was carried out, generating three samples of 450 data, each with calculated absolute differences.

Then, the three statistics were calculated for each sample:

$$d_m = \left| \frac{\sum_{i=1}^{n} d_i}{n} \right| \quad (1)$$

$$s_d = \sqrt{\frac{\sum_{i=1}^{n} (d_i - d_m)^2}{n-1}} \quad (2)$$

where the following results were obtained:

| Statistics | Sample 1 | Sample 2 | Sample 3 |
|---|---|---|---|
| $d_m$ | 3.026 | 2.866 | 2.852 |
| $s_d$ | 2.543 | 2.301 | 2.411 |

Then, the conditions $d_m$<4.602 beats/minute and $s_d$<4.718 beats/minute were applied, obtaining a successful result for said conditions.

Then, the t-Student test was applied to each sample:

$$\tau = \frac{d_m}{s_d} \sqrt{n} \quad (3)$$

obtaining the following results:

| Statistics | Sample 1 | Sample 2 | Sample 3 |
|---|---|---|---|
| $\tau$ | 26.600 | 27.840 | 26.439 |

Then, each calculated $\tau$ was compared to the t value in the t-Student test table; where, if $\tau$>2.55, it is concluded that there is not a significant difference between the preductal and the postductal blood flow (99% certainty); that is, heart rates are statistically similar and, therefore, the analyzed physiological data samples are considered as having approved the statistical validation.

Oxygen saturations corresponding to sample data may be considered for analysis through the critical congenital heart disease screening protocol defined by the American Academy of Pediatrics.

Additional Examples

The method of validation of the actual invention may also be exemplified in the clinic electromyography, which involves the record and analysis of the bioelectrical activity of the skeletal muscle in order to diagnose neuromuscular diseases. The variations with respect to normal electrical patters in each muscle, along with the assessment of other neurophysiologic data and the clinical context of each patient, constitute the protocol to which the results of the method are applied [2].

An additional example of the manner in which the actual invention may be applied is in the ankle-brachial index (AAI). The AAI is a non-invasive check-up that is useful for screening of the peripheral artery disease in most patients with diabetes. This index is calculated by dividing the systolic blood pressure at the ankle by the systolic blood pressure in the arm, and said index may be applied to reference values proposed by the American Association of Diabetes [3].

Finally, it should be understood that the method for the acquisition and validation of physiological data for medical devices of the actual invention is not limited exclusively to the embodiments described and illustrated herein, and that those with ordinary skills in the scientific, technical and/or medical field of the invention may, from the knowledge provided by the actual invention, make various modifications which shall clearly fall within the inventive concept and scope of the invention claimed by the following attached claims.

REFERENCES

1. Kemper A R, Mahle W T, Martin G R, et al. Strategies for Implementing Screening for Critical Congenital Heart Disease. Pediatrics. 2011; 128(5):e1259-e1267. doi: 10.1542/peds.2011-1317.
2. Gila L, Malanda A, Rodríguez Carreño I, Rodríguez Falces J, Navallas J. Métodos de procesamiento y análisis de señales electromiográficas. An Sist Sanit Navar. 2009; 32:27-43. doi:10.4321/S1137-66272009000600003.
3. Aboyans V, Criqui M H, Abraham P, et al. Measurement and Interpretation of the Ankle-Brachial Index: A Scientific Statement From the American Heart Association. Circulation. 2012; 126(24):2890-2909. doi:10.1161/CIR.0b013e318276fbcb.

The invention claimed is:
1. A method for the validation of physiological data, acquired in two or more parts of the human body by sensors connected to a medical device, for the statistical validation of the relationship among the data of the signals retrieved by said medical devices, said method comprising the steps of:
 a) verifying that sensors are connected to the medical device by information processing means, and that physiological data, consistent with the parameters sought to be measured, is recorded;
 b) defining the elapsed time of the study (Tt; starting at 0 seconds); the maximum time of the study (Tmax=specific time constant); the sampling time (Tm=specific time constant) during which the physiological data, needed for the statistical study, is collected; the reading time (TL=specific time constant), said reading time being the interval at which physiological data is retrieved from the communication port; the validation time (Tv), which defines the time at which statistical analysis is carried out, said validation time comprising one or more preset time values greater than Tm;
 c) retrieving physiological data separately from each of said two or more sensors by said information processing means within a preset reading time interval (TL);
 d) repeating step c) every TL until the following condition is met: Tt=Tv, and if this condition is met, proceeding to the next step;
 e) making a statistical validation of the physiological data retrieved from said two or more sensors, defined based on the volume and characteristics thereof, by the use of the information processing means;

f) if physiological data, acquired in this manner, does not approve the statistical validation made in step e) and Tt<Tmax, repeating steps c), d) and e);

g) if physiological data, acquired in this manner, does not approve the statistical validation made in step e), and Tt>=Tmax, concluding the method;

h) if physiological data, acquired in this manner, does approve the statistical validation made in step e), classifying said acquired data as being suitable for use and concluding the method.

2. The method for the acquisition and validation of physiological data in accordance with claim 1, wherein TL=1 second and Tm=60 seconds.

3. The method for the acquisition and validation of physiological data in accordance with claim 1, wherein said statistical validation comprises the compliance of two conditions and a parametric statistical test applied to the retrieved physiological data, wherein said statistical validation comprises the steps of:

I. calculating the absolute differences for each record of physiological data comprised within the time interval under analysis;

II. obtaining two or more random samples of the absolute differences previously calculated, wherein each sample includes 10% of the population of retrieved physiological data (n);

III. calculating the following statistics for each physiological data sample: (1) mean difference average ($d_m$), (2) standard deviation ($s_d$), and (3) t value of the statistical test known as t-Student for each sample ($\tau$) taken in sub-step ii, in accordance with the following formulas:

$$d_m = \left| \frac{\sum_{i=1}^{n} d_i}{n} \right| \quad (1)$$

$$s_d = \sqrt{\frac{\sum_{i=1}^{n} (d_i - d_m)^2}{n-1}} \quad (2)$$

$$\tau = \frac{d_m}{s_d} \sqrt{n} \quad (3)$$

IV. establishing the following conditions: $d_m$<'preset value' and $s_d$<'preset value';

V. if the conditions established in sub-step IV are met, comparing $\tau$ value (calculated in sub-step III) to the t value in the t-Student test table; where, if $\tau$>2.55, it is concluded that the acquired physiological data is statistically similar and, therefore, the analyzed physiological data samples are considered as having approved the statistical validation; otherwise, the analyzed physiological data samples are considered as having failed the statistical validation.

4. The method for the acquisition and validation of physiological data in accordance with claim 1, including the additional step of applying existing medical protocols/reference values to the physiological data that approved the statistical validation.

5. A method for the acquisition and validation of physiological data for use thereof with a physiological monitor for simultaneously taking oxygen saturation values in a human patient's preductal and postductal blood flow, wherein said physiological monitor comprises: two LED light-emitting/receiving sensors connected to a corresponding pulse oximeter to be placed on two or more parts of the patient's body, wherein each pulse oximeter is connected to information processing means, wherein the method for the acquisition and validation of physiological data comprises:

a) verifying that: sensors are connected to the medical device, that sensor receptor captures the light signal emitted by the sensor, and that the recorded physiological data is consistent with the heart rate readings;

b) upon successful conclusion of step a), beginning the study and establishing the following variables: elapsed time of the study (Tt; starting at 0 seconds); maximum time of the study (Tmax=specific time constant); sampling time (Tm=specific time constant) during which the physiological data, needed for the statistical study, is collected; reading time (TL=specific time constant), said reading time being the interval at which physiological data is retrieved from the communication port; validation time (Tv), which defines the time at which statistical analysis is carried out, said validation time comprising one or more preset time values greater than Tm;

c) retrieving physiological data (heart rate, oxygen saturation in preductal and postductal blood flow, as well as the values needed to generate a plethysmographic curve) separately and simultaneously from each of said two sensors and stored in the pulse oximeters by said information processing means within a preset reading time interval (TL);

d) repeating step c) every TL until the following condition is met: Tt=Tv, and if this condition is met, proceeding to the next step;

e) making a statistical validation of the heart rate values retrieved from said two sensors—where said information is stored in the pulse oximeters and retrieved by the information processing means—defined based on the volume and characteristics thereof, and comprising the following sub-steps:

i. calculating the absolute differences for each record of heart rates comprised within the time interval under analysis;

ii. obtaining two or more random samples of the maximum absolute differences previously calculated, wherein each sample includes 10% of the population of retrieved heart rate data (n);

iii. calculating the following statistics for each heart rate data samples: (1) mean difference average ($d_m$), (2) standard deviation ($s_d$), and (3) t value (of the statistical test known as t-Student) for each sample ($\tau$) taken in sub-step ii, in accordance with the following formulas:

$$d_m = \left| \frac{\sum_{i=1}^{n} d_i}{n} \right| \quad (1)$$

$$s_d = \sqrt{\frac{\sum_{i=1}^{n} (d_i - d_m)^2}{n-1}} \quad (2)$$

$$\tau = \frac{d_m}{s_d} \sqrt{n} \quad (3)$$

iv. applying the following conditions: $d_m$<'preset value' and $s_d$<'preset value', wherein said preset values for the present particular embodiment of the invention are: $d_m$<4.602 beats/minute and $s_d$<4.718 beats/minute;

v. if the established conditions are met in sub-step iv, comparing the τ value (calculated in sub-step III) to the t value in the t-Student test table; where, if τ>2.55, it is concluded that there is not a significant difference between the preductal and the postductal blood flow (99% certainty); that is, heart rates are statistically similar and, therefore, the analyzed heart rate data samples are considered as having approved the statistical validation; otherwise, the analyzed heart rate data samples are considered as having failed the statistical validation;

f) if heart rate data, acquired in this manner, does not approve step e), and Tt<Tmax, repeating steps c), d) and e);

g) if heart rate data, acquired in this manner, does not approve step e), and Tt>=Tmax, concluding the method;

h) if heart rate data, acquired in this manner, does approve step e), said heart rate data may be considered as being suitable for use.

6. The method for the acquisition and validation of physiological data in accordance with claim 5, wherein statistically validated measurement values may be automatically stored in the information processing means memory and hosted in an external server for further consultation thereof.

7. The method for the acquisition and validation of physiological data in accordance with claim 5, wherein statistically validated measurement values may be assessed by information procession means in accordance with a critical congenital heart defects screening protocol.

\* \* \* \* \*